(12) United States Patent
Eikmanns et al.

(10) Patent No.: US 7,267,967 B1
(45) Date of Patent: Sep. 11, 2007

(54) NUCLEIC ACID ENCODING PYRUVATE CARBOXYLASE FROM CORYNEFORM GLUTAMICUM

(75) Inventors: Bernd Eikmanns, Ulm (DE); Petra Peters-Wendisch, Bergisch-Gladbach (DE); Hermann Sahm, Jülich (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/529,043

(22) PCT Filed: Sep. 30, 1998

(86) PCT No.: PCT/EP98/06210

§ 371 (c)(1),
(2), (4) Date: Apr. 3, 2000

(87) PCT Pub. No.: WO99/18228

PCT Pub. Date: Apr. 15, 1999

(30) Foreign Application Priority Data

Nov. 4, 1997 (DE) ................................ 197 43 894
Jul. 14, 1998 (DE) ................................ 198 31 609

(51) Int. Cl.
C12P 13/04 (2006.01)
C12P 13/08 (2006.01)
C12P 13/06 (2006.01)
C12P 13/14 (2006.01)
C12N 15/00 (2006.01)
C12N 1/20 (2006.01)

(52) U.S. Cl. ................ 435/106; 435/320.1; 435/252.3; 435/252.32; 435/115; 435/116; 435/110

(58) Field of Classification Search ................ 536/23.2; 435/199, 320.1, 325, 419, 252.32, 254.11
See application file for complete search history.

(56) References Cited

FOREIGN PATENT DOCUMENTS

| EP | 0 358 940 A1 | 3/1990 |
| EP | 0 358 940 B1 | 9/1995 |
| EP | 0 551 614 B1 | 4/1996 |
| EP | 0 723 011 A1 | 7/1996 |

OTHER PUBLICATIONS

Eikmanns et al. Antonie Van Leeuwenhoek (1993-94) 64(2):145-163.*
De Boer et al. Proc Natl Acad Sci USA (1983) 80(1):21-25.*
Koffas et al. Appl Microbiol Biotechnol (1998) 50(3):346-352.*
Wolf-Dieter Deckwer et al. "Biotechnologie and Gentechnik", Georg Thieme Verlag, Stuttgart, Germany, 1999.*
Branden et al. "Introduction to Protein Structure", Garland Publishing Inc., New York, 1991, p. 247.*
Witkowski et al. (1999) Biochemistry 38:11643-11650.*
Guo et al. PNAS (2004) 101:9205-9210.*
GenBank Accession No. P95127, May 1, 1997.*
"Recombinant DNA Methodology," Dillon, John Wiley and Sons, Inc., New York, 1985, pp. 81-83.*
Meadow et al. Biochem J 72:400-407, 1959.*
Gubler et al. App Environ Microbiol 60 :2494-2500, 1994.*
Seep-Feldhaus et al., Mol Microbiol 5:2995-3005, 1991.*
Han et al., Mol Microbiol 4:1693-1702, 1990.*
Cohen et al., J. Bacteriol 99:791-801, 1969.*
Arch. Microbiol. (1996) 165:387-396 "C3 Carboxylation as an anaplerotic reaction . . ."
ST International WPINEX File Search Results—S950040K of Aug. 9, 1996.
FEMS Microbiology Letters 112 (1993)269-274 "Phosphoenolpyruvate carboxylase . . ."
"Anaploroti reactions in Corynebacterium glutamicum" by P. Peters-Wendisch Copyright (c) 1998 Am. Chem Soc.
"Pyruvate carboxylase as an anaplerotic enzyme . . ." by P. Peters-Wendisch, Microbiology (1997) 143, 1095-1103.
Petra Peters-Wendisch; pp. 81-102 Aug. 1996 Institut fur Biotechnologie; Fors. Julich GmbH; Anaplerotische Reaktionen in *Corynebacterium glutamicum*: Untersuchungen zur Bedeutung der PEP-Carboxylase und der Pyruvat-Carboxylase im Zentralstoffwechsel und bel der Aminosaure-Produktion.

* cited by examiner

*Primary Examiner*—David J. Steadman
(74) *Attorney, Agent, or Firm*—Jonathan Myers; Andrew Wilford (57) ABSTRACT

A pyruvate carboxylase gene having SEQ ID NO:1 as well as an amino acid sequence having SEQ ID NO:2 expressed by the pyruvate carboxylate gene are disclosed. Also disclosed is a method for microbial production of amino acids of the aspartate and/or glutamate family in which the pyruvate carboxylase activity is increased by genetically changing the pyruvate carboxylase gene having SEQ ID NO:1 through expression of a microorganism which produces the corresponding amino acid having SEQ ID NO:2.

5 Claims, 2 Drawing Sheets

NUCLEIC ACID ENCODING PYRUVATE CARBOXYLASE FROM CORYNEFORM GLUTAMICUM

FIELD OF THE INVENTION

The invention relates to a method of microbial production of amino acids of the aspartate family and/or of the glutamate family, to the pyruvate-carboxylase gene and to gene structures, vectors and transformed cells containing the pyruvate carboxylate gene.

BACKGROUND OF THE INVENTION

Amino acids are of considerable economic interest since amino acids have many uses: thus, for example, L-lysine and L-threonine, L-methionine and L-tryptophan are necessary as fodder additives, L-glutamate as an additive to suppress L-isoleucine and L-tyrosine in the pharmaceutical industry, L-arginine and L-isoleucine as medicaments or L-glutamate, L-aspartate and L-phenylalanine as starting substances for the synthesis of fine chemicals.

A preferred method of producing these different amino acids is the biotechnical production by means of microorganisms such that in this manner the biologically-effective and optically-active forms of the respective amino acids are obtained and simple and inexpensive raw materials can be used. As microorganisms, for example, *Corynebacterium glutamicum* and its derivatives sap. *Flavum* and ssp. *Lactofermentum* (Liebl et al., Int J System Bacteriol 1991, 41: 255 to 260) in addition to *Escherichia coli* and related bacteria are used. These bacteria normally produce the amino acids but only in amounts required for growth so that no surplus amino acids are formed and can be recovered. This is because in the cells the biosynthesis of amino acids is controlled in many ways. As a consequence, there are already known various processes to increase the product formation by cutting out the control mechanisms. In these processes, for example, amino acid analogs are introduced to switch off the effective regulation of the biosynthesis. For example, a process has been used which is resistant to L-tyrosine analogs and L-phenylalanine analogs (JP 19037/1976 and 39517/1978). The processes also have been described in which bacteria resistant to L-lysine analogs or L-phenylalanine analogs have been used to suppress the control mechanisms (EP 0 205 849, GB 2 152 509).

Furthermore, microorganisms which have been constructed also by recombinant DNA-techniques obviate regulation of biosynthesis in that the gene which is coded in the no-longer feedback-inhibited key enzyme is cloned and expressed. For example, the recombinant L-lysine-producing bacterium with plasmid-coded feedback-resistant aspartate kinase is known (EP 0 381 527). In addition, a recombinant L-phenylalanine-producing bacterium with feedback-resistant prephenate dehydrogenase is described (JP 123475/1986, EP 0 488 424).

In addition, by overexpression of genes which do not code for feedback-sensitive enzymes in amino acid synthesis, increased amino acid yields are obtainable. Thus, for example, lysine formation can be improved by increased synthesis of the dihydrodipicolinate synthesis (EP 0 197 335). Increasingly, by increased synthesis of the threoninedehydratease, improved isoleucine formation is achieved (EP 0 436 886).

Further investigations in increasing amino acid production have been targeted on the improved availability of the cellular primary metabolites of central metabolism. Thus it is known that, by recombinant techniques, over-expression of the transketolase can bring about an improved product formation of L-tryptophan or L-tyrosine or L-phenylalanine (EP 0 600 463). Furthermore, a reduction of the phosphoenolpyruvate-carboxylase activity in *Corynebacterium* leads to improved formation of aromatic amino acids (EP 0 3331 145) whereas by contrast an increase in the phosphoenolpyruvate-carboxylase activity in *Corynebacterium* leads to increased recovery of amino acids of the aspartate family (EP 0 358 940).

During the growth and especially under amino acid production conditions, the tricarboxylic acid cycle must continuously and effectively be supplemented with C4 compounds, for example, oxalic acetate to replace intermediate products withdrawn for the amino acid biosynthesis. Until recently it has been thought that phosphoenolpyruvate-carboxylase was responsible for these so-called anaplerotic functions in *Corynebacterium* (Kinoshita, Biology of Industrial Micro-organisms 1985: 115 to 142, Benjamin/Cummings Publishing Company, London; Liebl, The Prokaryotes II, 1991 to 1171, Springer Verlag N.Y.; Vallino and Stephanopoulos, Biotechnol Bioeng 1993, 41: 633 to 646).

It has, however, now been found that phosphoenolpyruvate-carboxylase-negative mutants grow equally by comparison to the respective starting strains on all media (Peters-Wendisch et al., FEMS Microbiology Letters 1993, 112: 269 to 274; Gubler et al., Appl Microbiol Biotechnol 1994, 40: 857 to 863). These results indicate that the phosphoenolpyruvate-carboxylase is not essential for the growth and plays no role or only a small role for the anaplerotic reactions. Furthermore the aforementioned results indicate that in *Corynebacterium* another enzyme must be provided which is responsible for the synthesis of oxalacetate which is required for growth. Recently, indeed, a pyruvate-carboxylase activity has been found in permeablized cells of *Corynebacterium glutamicum* (Peters-Wendisch et al., Microbiology 1997, 143: 1095 to 1103). This enzyme is effectively inhibited by AMP, ADP and acetyl coenzyme A and in the presence of lactate as a carbon source is formed in increased quantities. Since one must conclude that this enzyme is answerable primarily for the satisfaction of the tricarboxylic acid cycle of growth, it was to be expected that an increase in the gene expression or the enzymatic activity would either give rise to no increase in the amino acids belonging to the aspartate or yield only an increase therein. Furthermore, it was to be expected that an increase in the gene expression or the enzymatic activity of the pyruvate-carboxylase would also have no influence on the production of amino acids of other families.

SUMMARY OF THE INVENTION

It has surprisingly been found that an increase in the pyruvate-carboxylase activity by genetic modification of the enzyme and/or by increasing the pyruvate-carboxylase gene expression, the microbial production of amino acids of the aspartate and/or the glutamate families can be increased. It has been found that especially strains with increased copy numbers of the pyruvate-carboxylase gene can produce about 50% more lysine, 40% more threonine and 150% more homoserine in the culture medium. It has been found further that, surprisingly, the glutamate production is also significantly increased (compare especially the example under 6. Table 4).

The genetic alteration of the pyruvate-carboxylase to increase the enzyme activity is effected preferably by mutation of the endogenous gene. Such mutation can either be achieved by classical methods like, for example, by UV irradiation or by mutation triggering the chemicals or targeted by means of gene technological methods like deletion, insertion and/or nucleotide exchange.

The pyruvate-carboxylase gene expression is increased by increasing the gene copy number and/or by reinforcing regulatory factors which positively influence the expression of the gene. Thus a reinforcement of regulatory elements, preferably on the transcription plane can be effected in that especially the transcription signals are increased. This can be effected, for example, by varying the promoter sequence of the promoter preceding the structure gene to enhance its effectiveness or by replacing the promoter completely by more effective promoters. A reinforcement of the transcription can also be effected by a corresponding influence on a regulator gene associated with the pyruvate-carboxylase gene. This can be achieved, for example, by mutation of a regulatory gene sequence to influence the effectivity of the binding of a regulator protein to the DNA of the pyruvate-carboxylase gene which is regulated so that the transcription is thereby enhanced and thus the gene expression is increased. Furthermore the pyruvate-carboxylase gene can also be associated with a so-called "enhancer" as a regulatory sequence and which by means of an improved interchange between RNA polymerase and DNA also effects an increased pyruvate-carboxylase gene expression. However, a reinforcement of translations is also possible in that, for example, the stability of the m-RNA is improved.

For increasing the gene copy number the pyruvate-carboxylase gene is built into a gene construct or vector. The gene construct contains especially the regulatory sequences associated with the pyruvate-carboxylase gene, preferably those which reinforce the gene expression. For the incorporation of the pyruvate-carboxylase gene in a gene construct, the gene is progressively isolated from a microorganism strain of the *Corynebacterium* variety and is transformed in an amino-acid producing microorganism strain, especially *Corynebacterium* or in *Escherichia coli* or *serratia marcenscens*. For the process of the invention, especially genes from *C. glutamicum* or *C. glutamicum* ssp. *flavum* or *C. glutamicum* ssp. *lactofermentum* are suitable. After isolation of the gene and in the in vitro recombination with known vectors (see for example Simon et al., Bio/Technology 1983, 1: 784 to 791; Eikmanns et al., Gene 1991, 102: 93 to 98), the transformation is effected in the amino-acid producing strain by electroporation (Liebl et al., FEMS Microbiology Letters 1991, 65: 299 to 304) or conjugation (Schafer et al., J. Bacteriol 1990, 172: 1663 to 1666).

As the host strain preferably such amino-acid producers are used which have been deregulated in the synthesis of the corresponding amino acid and/or show an increased export carrier activity for the corresponding amino acid. Furthermore, such strains are preferred which contain an increased number of such central metabolism metabolites as anticipated in the synthesis of the corresponding amino acid and/or strains which contain a reduced proportion of the central metabolism metabolites which do not participate in the synthesis of the corresponding amino acid, especially metabolites which tolerate competitive reactions; i.e. such strains are preferred in which synthesis paths competitive with the corresponding amino acid biosynthesis path run with reduced activity. Thus, especially a Coryne-former microorganism strain with reduced citrate synthase activity is suitable as a strain resistant to L-asparaginic-acid-β-methylester (AME) (EP 0 551 614).

After isolation, the pyruvate-carboxylase gene is obtained with nucleotide sequences which code for the amino acid sequence given under SEQ ID NO. 2 or their allele variations or the nucleotide sequence of nucleotides 165 to 3587 according to SEQ ID NO. 1 or a substantially identically-effective DNA sequence. The gene further contains a protein promoter of the nucleotide sequence of nucleotides 20 to 109 according to SEQ ID NO. 1, a substantially identically effective DNA sequence. Allele variations or identically effective DNA sequences encompass especially functional derivations which are corresponding nucleotide sequences formed by deletions, insertions and/or substitutions of nucleotides whereby the enzyme activity or function remains or can even be increased. This pyruvate-carboxylase gene is preferably used in the process of the invention.

The pyruvate-carboxylase gene with or without the preceding promoter or with or without the associated regulator gene can be preceded by and/or followed by one or more DNA sequences so that the gene is contained in a gene structure.

The pyruvate-carboxylase gene is preferably preceded by the tac-promoter (lacI$^Q$-Gen) which is associated especially with regulatory sequences.

By cloning the pyruvate-carboxylase gene, plasmids are obtained which contain the gene and are suitable for transformation to an amino acid producer. The cells obtained by transformation which preferably correspond to transformed cells of *Corynebacterium*, contain the gene in replicatable form, i.e. in additional copies on the chromosome, whereby the gene copies are integrated by recombination at optional sites in the genome and/or on a plasmid or vector.

EXAMPLE

1. Cloning the Pyruvate-Carboxylase Gene of *Corynebacterium Glutamicum*

Starting from conserved regions of all prior known pyruvate-carboxylase-(pyc-) genes of *Saccharomyces cerevisiae* (J Biol Chem 1988, 263: 11493-11497; Mol Gen Genet 1991, 229: 307-315), Mensch (Biochem Biophys Acta 1994, 1227: 46-52), Maus (Proc Natl Acad Sci, USA 1993, 90: 1766-1770), *Aedes aegypti* (EMBL-GeneBank: Accession Nr. L36530) and from *Mycobacterium tuberculosis* (EMBL-GeneBank: Accession Nr. U00024), PCR primer is synthesized (MWG Biotech). The primer corresponds to the bases 810 to 831 and 1015 to 1037 of the pyc gene from *M. tuberculosis*. With this primer, by means of PCR according to the standard method of Innis et al (PCR protocols. A Guide to Methods and Applications, 1990, Academic Press) for nongenerated homologous primer, a fragment of about 200 bp of chromosomal DNA of *C. glutamicum* ATCC 13032 as has been described by Eikmanns et al. (Microbiology 1994, 140: 1817-1828) is isolated following amplification. The size of 200 bp corresponds to the expectation for the pyc gene. The PCR product as described by Sanger et al (Proc Natl Acad Sci USA 1977, 74: 5463-5467) was sequenced. The sequencing was carried out with fluorescence-marked ddNTPs with an automatic DNA sequencing apparatus (Applied Biosystems).

Starting from this DNA fragment of C. glutamicum, the following homologous oligonucleotides are produced:

```
pyc 1    5'-CGTCTTCATCGAAATGAAC-3'    SEQ ID NO:3
pyc 2    5'-ACGGTGGTGATCCGGCACT-3'    SEQ ID NO:4
```

The oligonucleotide is used as a PCR primer for isolating the probe for the gene of pyruvate-carboxylase (pyc) from C. glutamicum. The primer is introduced into a PCR reaction with chromosomal DNA from C. glutamicum and digoxygenine-marked nucleotides. The reaction is carried out in accordance with the instructions of the "PCR DIG Labeling Kits" of the firm Boehringer Mannheim. With this approach, a digoxygenine-marked DNA fragment is amplified which corresponds to the expected size of about 200 bp. The thus produced pyc probe is then used to identify, utilizing Southern-blot-hybridization, A DNA fragment in the chromosomal DNA of C. glutamicum on which the pyc gene is localized. For this purpose each 2 to 5 μg of chromosomal DNA from C. glutamicum WT is cleaved with the restriction enzyme HindIII, SphI, SalI, DdraI, EcoRI and BamHI and the obtained DNA fragments are correspondingly separated by size over 16 hours at 20 volts gel-electrophoretically in an 0.8% agarose gel. The DNA fragments found in the agarose gel are denatured by the Southern blot (J Mol Biol 1975, 98: 503-517) and subjected to the vacuum-supported separation with the VacuGene Blot Apparatus of Pharmacia LKB (Uppsala, Sweden) from the gene matrix transferred onto a nylon membrane (Nytran N13 of Schleicher and Schüll, Dassel, Switzerland), immobilized and the digoxygenine marker detected by means of NBT/X phosphate conversion with alkali phosphatizes in this manner. The following chromosomal fragments hybridized with the pyc-DNA-probe can be detected: a 17 kb HindIII-fragment, a 6.5 kb SalI fragment and a 1.35 kb EcoRI fragment.

The 17 kb HindIII fragment was isolated and subcloned. For this purpose a cosmid gene bank of chromosomal DNA from C. glutamicum in cosmid pH C79 was used which represented the genome of C. glutamicum to 99% (Mol Microbiol 1992, 6: 317-326). The E. coli strain DH5α was transformed with this gene bank by means of the CaCl₂ method of Sambrook et al (Molecular Cloning, A Laboratory Manual, 1989, Cold Spring Harbor Laboratory Press) and plated out to about 300 colonies per LB-agar plate with 50 μg/l kanamycin (a total of 5000 colonies). Then the obtained transformed product was transferred on a nytran N13 filter and incubated for 5 minutes for alkali lysis of the cells and denaturing of the DNA on Whatmann paper soaked with 0.5 M NaOH and 1.5 M NaCl. The subsequent neutralization is effected with 1 M Tris/HCl pH 7.5 and 1.5 M NaCl. The subsequent neutralization is effected with 1 M Tris/HCl pH 7.5 and 1.5 M NaCl.

After incubation of the filter in 2×SSC, the liberated DNA is fixed by UV radiation at 366 nm on the filter. Then the remaining cell fragments are removed by shaking in 3×SSC, 0.1% SDS at 50° C. The filter in this form is used for the hybdridiza-tion with a specific pyc probe as described by Southern (J Mol Biol 1975, 98: 503-517).

Figure 1:
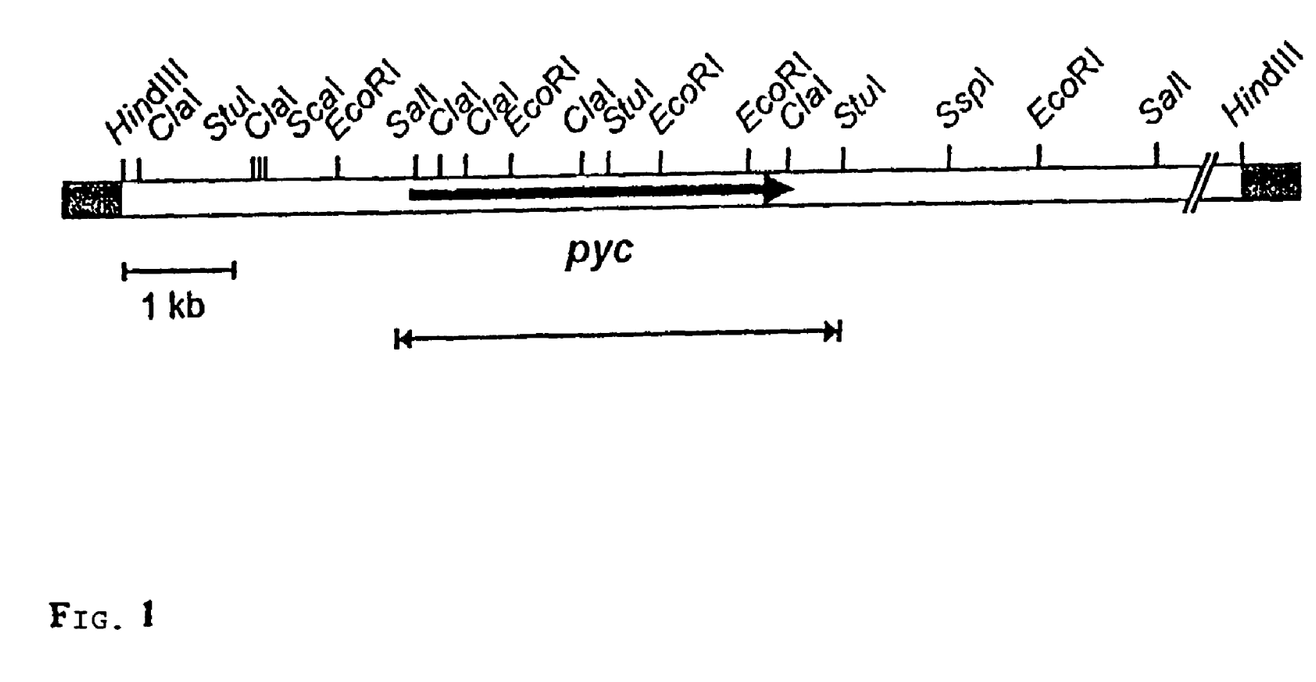
FIG. 1 is a physical map and restriction analysis of the cloned pyruvate carboxylase encoding gene from *C. Glutamicum* ATCC 13032 in pUC18 resulting in the vector pUCpyc.

The 3 transformants were identified from the pyc probe hybridization. From these transformants the cosmid DNA was isolated by means of plasmid proportion in accordance with the alkali lysis method of Birnboim (Meth Enzymol 1983, 100: 243-255) and then tested by restriction and Southern blot analysis for the presence of the HINDIII fragments. The cosmid pH C79-10 which contains a 40 kb HINDIII transmission completely and was further analyzed. It showed that also after the restriction with the endonucleosis SalI and EcoRI the same hybridized fragments as in the chromosomal DNA, i.e. a 6.5 kb SalI-fragment and a 1.35 kb EcRI-fragment. The 17 kb HindIII-fragment was isolated by restriction from the cosmid and is ligated in the E. coli vector pUC 18, which is also cleaved with HindIII. A restriction analysis of the fragments in the resulting vector pUC pyc was carried out. The physical mapping of the fragments is shown in FIG. 1.

2. Sequencing of the Pyruvate-Carboxylase Gene

In further subcloning steps a 0.85 kb SalI-EcoRI-fragment was isolated from the plasmid pUC pyc by restriction with corresponding restriction enzymes as a 1.35 kb EcoRI-fragment, a 1.6 kb EcoRI-EcoRI-StuI-fragment as well as a 1.6 kb ClaI-fragment, that overlapped with 0.85 kb SalI-EcoRI-fragment. By ligation the fragments were cloned correspondingly in the restricting vector pUC 18 and then sequenced as described above according to Sanger et al. In (Proc Natl Acad Sci USA 1977, 74: 5463-5467) the nucleotide sequences obtained were analyzed. The program package HUSAR (Release 3.0) of the German zone for cancer research (Heidelberg). The sequence analysis of the fragments gave a continuously open reading raster of 3576 bp which coded for a protein sequence of 1140 amino acids. Comparison of the protein sequence with the EMBL gene data bank (Heidelberg) gave similarities to all known pyruvate carboxylases. The highest identity (62%) was to the putative pyruvate-carboxylase from Mycobacterium tuberculosis (EMBL-GeneBank: Accession No. U00024). The similarity amounted to 76% when conserved amino acid exchange was followed. A comparison with the pyruvate-carboxylase of other organisms yielded an identity of 46 to 47% identical and 64 to 65% similar amino acids (Gene 1997, 191: 47-50; J Bacteriol 1996, 178: 5960-5970; Proc Natl Acad Sci USA 1993, 990: 1766-1770; Biochem J 1996, 316: 631-637; EMBL-GenBank: Accession No. L36530; J Biol Chem 1988, 263: 11493-11497; Mol Gen Genet 1991, 229: 307-315). From these results it could be concluded that the cloned fraction base was the gene for the pyruvate-carboxylase from C. glutamicum. The nucleotide sequence of the gene is given under SEQ ID NO: 1 and the corresponding amino acid sequence under SEQ ID NO: 2.

3. Overexpression of the Pyruvate-Carboxylase

For the overexpression of the gene for pyruvate-carboxylase from C. glutamicum, the gene was cloned from the plasmid pUCpyc as the 6.2 kb Sspl-ScaI-fragment in the E. coli glutamicum swing vector pEK0 (Gene 1991, 102: 93-98) which was cleaved with the restriction endonucleosis EcoRI and PstI. By means of Klenow-polymerase treatment the overhanging ends were ligated to smooth ends by filling the EcoRI or linking PstI and the linearized vector was ligated with the 6.2 kb Sspl-Scal-fragment. The resulting construct pEK0pyc was additionally transformed in the E. coli strain DH5α, the plasmid DNA was isolated on the resulting transformand and the correctness of the inserts controlled by restriction. The DNA was then introduced in the strain SP 733 by electroporation (FEMS Microbiol Lett 1989, 65: 299-304).

This strain is a mutant of the restriction negative *C. glutamicum* strain R 127 (Dechema Biotechnology Conference 1990, 4: 323-327, Verlag Chemie) which was obtained by chemical mutagenesis and was characterized in that it cannot be grown on a minimal medium with pyruvate and lactate as single carbon sources (Microbiology 1997, 143: 1095-1103). This phenotype is recognized as a defect in the pyruvate-carboxylase and can be complemented by introducing the pyruvate-carboxylase gene from *C. glutamicum*, i.e. the strain which is carried by the plasmid pEK0pyc and was by contrast to the starting strain able to grow again in the presence of minimal medium with lactate as a single carbon source. This was a verification that the gene was coded for a functional pyruvate-carboxylase.

Furthermore, the plasmid pEK0pyc was transformed in the *C. glutamicum* wild type ATCC 13032 by electroporation. The resulting strain WT (pEK0pyc) was investigated by comparison to the wild type ATCC 13032 with respect to its pyruvate-carboxylase activity. The strain was cultured in a complex medium (Luria-Bertani, Molecular Cloning, A laboratory manual, 1989, Cold Spring Harbor Laboratory Press) with 0.5% lactate and on minimal medium with 2% lactate or 4% glucose and the pyruvate-carboxylase test was carried out corresponding to the method as described by Peters-Wendisch et al (Microbiology 1997, 143: 1095-1103). The results of the analysis (Table 1) showed that the pyruvate-carboxylase activity in the pEK0-pyc-carrying strain was about 4 times higher than in the starting strain.

4. Increased Accumulation of Lysine by Overexpression of the Pyruvate-Carboxylase Gene in the Strain C-glutamicum DG 52-5

Figure 2:
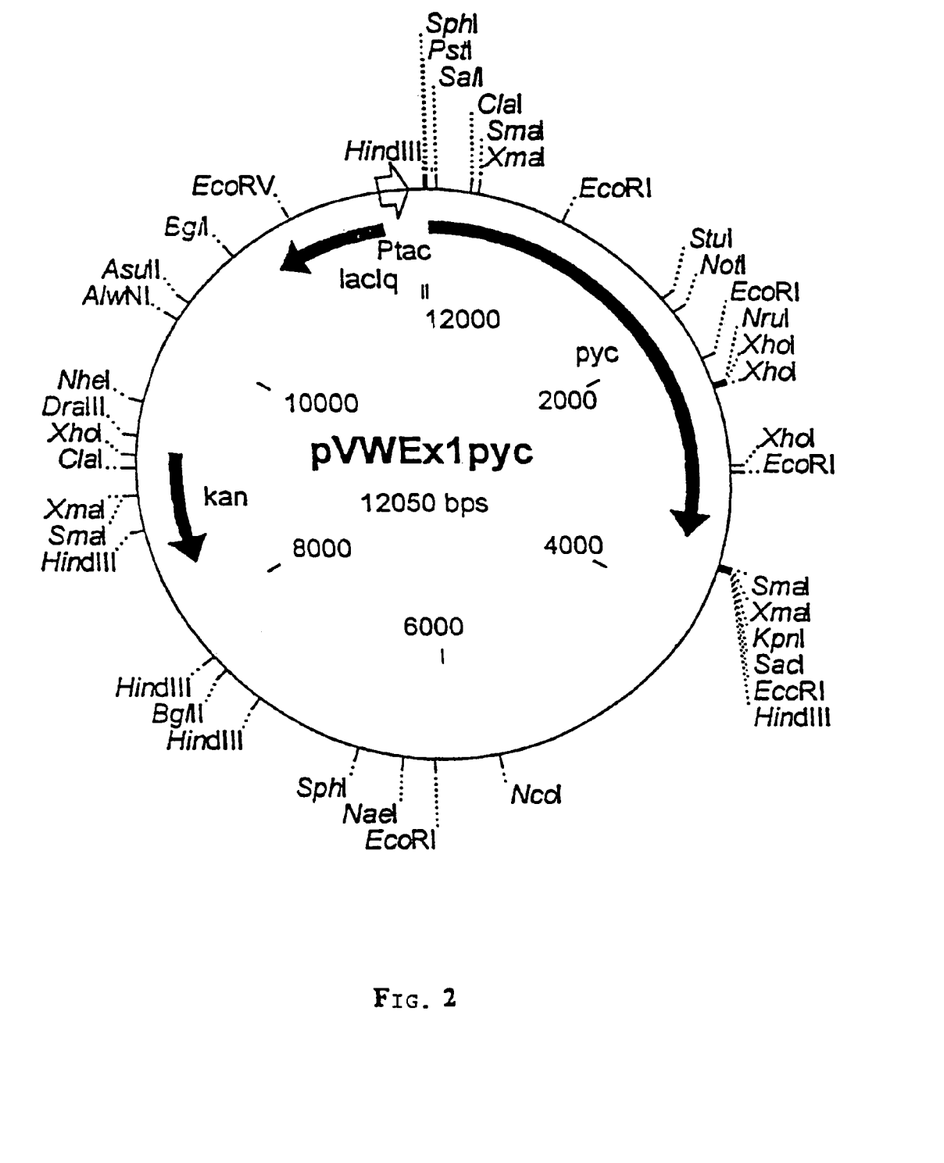
FIG. 2 is a physical map of the expression vector pUWEX1 containing the pyruvate carboxylase encoding gene from *C. glutamicum* 13032. Abbreviations: pvc=pyruvate carboxylase, Ptac-IPTG-inducibe synthetic promoter of trp- (−35 box) and lac-promoter (−10 box) regions; laclq-gene encoding the repressor of lac operon, kan-gene encoding the resistance to kananycin.

To investigate the effect of the overexpression of the gene for the pyruvate-carboxylase in the lysine-producing strain DG 52-5 (J Gen Microbiol 1988, 134: 3221-3229), the expression vector pVWEX1 is used to promote an IPTG-inducible expression. In this vector, the pyc gene was promotorlessly cloned. For that purpose, initially PCT-Primer (Primer 1=Postion 112-133; Primer 2=Position 373 to 355 in the nucleotide sequence according to SEQ ID NO. 1), is synthesized and 261 bp of the promotorless starting region of the pyruvate-carboxylase gene was amplified by means of PCR. The primer was so selected that Primer I enabled a PstI cleavage site and Primer 2 a BamHI cleavage site. After the PCR, the 274 bp PCR product was isolated, ligated to concatemers and then cleaved with the restriction enzymes PstI and BamHI. The restriction product was concentrated by ethanol precipitation and then ligated with the PstI-BamHI cleaved vector pVWEX1. The resulting construct pVWEXi-PCR was tested by restriction. The end region of the pyc gene was isolated by RcaI-Klenow-SalI treatment from the vector pEK0pyc and ligated in the BamHI-Klenow-SalI during vector PVWEX1-PCR. The resulting construct pVWEX1pyc was analyzed by restriction mapping. Physical mapping of the plasmid is shown in FIG. 2.

The plasmid was introduced by electroporation in the *C. glutamicum* strain DG 52-5. As a control, the strain DG 52-5 was transformed with the vector pVWEX1 without insert and the L-lysine precipitation of three different transformands was compared. For this purpose (DG 52-5 (pVWEX1pyc) 3,4 and (2xTY; Molecular Cloning, A laboratory manual, 1989, Cold Spring Harbor Laboratory Press with 50 μg/I kanamycin) and the respective fermentation medium in each case from the preculture was separately inoculated. The medium contained additional kanamycin to maintain the plasmid stable. In each case two parallel tests were run whereby one flask of 200 μg IPTG/ml was added while the second flask contained no IPTG. After cultivation for 48 hours at 30° C. on a rotation shaker at 120 RPM, the accumulated lysine quantity in the medium was determined. The determination of the amino acid concentration was effected by means of high-pressure liquid chromatography (J Chromat 1983, 266; 471-482).

The results of the fermentation are shown in Table 2 whereby the values given are mean values each from three experiments with different clones. It shows that the overexpression of the pyruvate-carboxylase gene results in a 50% increased accumulation of lysine in the medium. Thus the use of the covered and described gene for the anapleurotic enzyme pyruvate-carboxylase enables a process of lysine formation to be significantly improved.

5. Increased Accumulation of Threonine and Homoserine by Overexpression of the Pyruvate-Carboxylase Gene in the Strain *C. glutamicum* DM 368-3

Analogously to the experiment in L-lysine formation, the accumulation of threonine in the culture supernatant by overexpression of the gene for pyruvate-carboxylase was also investigated for this purpose, as has been described under point 4, the threonine production strain *C. glutamicum* DM 368-3 (Degussa AG) was transformed with the plasmid pVWEX1pyc with control by the plasmid pVWEX1 and the threonine separation was investigated with each of three different transformands. For this purpose DM 368-3 (pVWEX1) 2 and 3 and DM 368-3 (pVWEX1pyc) 1, 2 and 3 in complex medium (2xTY with 50 μg/l kanamycin) were cultured and the fermentation medium CGXII (J Bacteriol 1993, 175: 5595-5603) in each case was separately inoculated from the preculture. The medium contained additional kanamycin to hold the plasmid stable. Two parallel sets of tests were carried out whereby 200 μg IPTG/ml was added to one flask while the second flask contained no IPTG. After culturing for 48 hours at 30° C. on a rotation shaker at 120 RPM, the threonine quantities accumulated in the medium were determined. The determination of the amino acid concentration was effected also by means of high-pressure liquid chromatography (J Chromat 1983, 266: 471-482). The results of the fermentation are shown in Table 3 whereby the values given are mean values from each of three experiments with different clones. It shows that the overexpression of the pyruvate-carboxylase gene gave about a 40% increase in the threonine concentration in the medium. The use of the covered and described gene for anapleurotic enzyme pyruvate-carboxylase in a process for L-threonine formation significantly improves the latter.

Furthermore, the amino acid concentration determination shows surprisingly that the strain with the overexpressed pyruvate-carboxylase gene also yields 150% more homoserine in the medium than the strain with the nonoverexpressed gene. Corresponding results are shown in Table 3. They make clear that in the process according to the invention the threonine yield like the homoserine yield can be significantly improved.

6. Increased Accumulation of Glutamate by Overexpression of the Pyruvate-Carboxylase Gene in *C. glutamicum* Wild Type Analogous to the experiments for L-lysine, L-threonine and L-homoserine formation (see above, the 4. and 5.), accumulation of glutamate in the culture supernatant, overexpression of the gene for pyruvate-carboxylase was also investigated. For this purpose, as described, the point 4 wild type C-glutamicum ATCC 13032 with the plasmid pVWEX1 pyc was transformed in addition to the control with the plasmid pVWEX1 and the glutamate separation determined from each of two different transformands. Thus *C. glutamicum* ATCC 13032 pVWEX1pyc) D1 and D2 as well as *C. glutamicum* ATCC 13032 (pVWEX1 pyc) 1 and 2 were cultured in the complex medium (2xTY with 50 µg/l kanamycin) and the fermentation medium CGXII (J Bacteriol 1993, 175: 5595-5603) in each case was separately inoculated from the preculture period. The medium contained additional kanamycin to stabilize the plasmid. To induce glutamate separation, 25 mg Tween 60 was added per ml to the medium about 6 hours after the inoculation. Two parallel sets of tests were carried out whereby in one, 200 µg IPTG/ml is added to the flask while the second flask contained no IPTG. After culturing for 48 hours at 30° C. on a rotation shaker at 120 RPM, the glutamate quantity accumulated in the medium was determined. The determination of the amino acid concentration was effected also by means of high-pressure liquid chromatography (J Chromat 1983, 266; 471-482). The results of the fermentation are shown in Table 4 whereby values given are averages with each two experiments with different clones. It shows that the overexpression of the pyruvate-carboxylase gene gave rise to up to 500% increase of the glutamate concentration in the medium. The use of the covered and described gene for the anapleurotic enzyme pyruvate-carboxylase improved the glutamate formation significantly.

TABLE 1

| Strain | IPTG [µg/ml] | Pyruvate Carboxylase [nmol min$^{-1}$ mg Dry Weight$^{-1}$] |
|---|---|---|
| 13032(pEK0pyc) | 0 | 75 ± 13 |
| ATCC 13032 | 0 | 19 ± 4 |
| DG52-5(pVWEX1pyc) | 200 | 88 ± 13 |
|  | 0 | 11 ± 2 |
| DG52-5(pVWEX1) | 200 | 5 ± 2 |
|  | 0 | 6 ± 1 |

TABLE 1-continued

| Strain | IPTG [µg/ml] | Pyruvate Carboxylase [nmol min$^{-1}$ mg Dry Weight$^{-1}$] |
|---|---|---|
| DM368-3(pVWEX1pyc) | 200 | 76 ± 10 |
|  | 0 | 12 ± 3 |
| DM368-3(pVWEX1) | 200 | 10 ± 1 |
|  | 0 | 11 ± 2 |

TABLE 2

| Strain | IPTG [µg/ml] | Lysine [mM] |
|---|---|---|
| DG52-5(pVWEX1pyc) | 200 | 35.4 ± 2.6 |
|  | 0 | 23.6 ± 2.9 |
| DG52-5(pVWEX1) | 200 | 23.3 ± 2.9 |
|  | 0 | 22.1 ± 4.0 |

TABLE 3

| Strain | IPTG [µg/ml] | Threonine [mM] | Homoserine [mM] |
|---|---|---|---|
| DM368-3(pVWEX1pyc) | 200 | 10.2 ± 0.5 | 14.4 ± 1.2 |
|  | 0 | 7.9 ± 1.0 | 5.6 ± 0.2 |
| DM368-3(pVWEX1) | 200 | 8.0 ± 0.5 | 5.5 ± 0.7 |
|  | 0 | 7.5 ± 0.8 | 6.1 ± 1.0 |

| Strain | IPTG [µg/ml] | Glutamate [mM] |
|---|---|---|
| ATCC 13032 | 200 | 11 ± 2 |
| ATCC 13032 | 0 | 13 ± 2 |
| ATCC 13032(pVWEX1-pyc) | 200 | 67 ± 4 |
| ATCC 13032(pVWEX1-pyc) | 0 | 32 ± 4 |

What is claimed is:

1. A pVWEX1pyc vector contained in the bacterium deposited under DSM 12893.

2. A bacterium comprising the vector of claim 1.

3. A method of microbially producing L-amino acids of aspartate and/or glutamate families, which comprises the step of:
   culturing an amino acid producing microorganism strain in a medium suitable for the production of an L-amino acid, whereby said amino acid producing microorganism strain is transformed with the vector pVWEX1pyc encoding the polypeptide comprising the amino acid sequence having SEQ ID NO:2 with pyruvate carboxylase activity.

4. The method of microbially producing L-amino acids as defined in claim 3 wherein the L-amino acid is selected from the group consisting of L-lysine, L-threonine, L-homoserine and L-glutamate.

5. The method of microbially producing L-amino acids as defined in claim 3 wherein said amino acid producing microorganism strain is *Corynebacterium glutamicum*.

* * * * *

SEQUENCE LISTING

<160> NUMBER OF SEQ ID NOS: 4

<210> SEQ ID NO 1
<211> LENGTH: 3728
<212> TYPE: DNA
<213> ORGANISM: Corynebacterium glutamicum
<220> FEATURE:
<221> NAME/KEY: CDS
<222> LOCATION: (165)..(3587)
<223> OTHER INFORMATION: pyruvate carboxylase

<400> SEQUENCE: 1

```
cgcaaccgtg cttgaagtcg tgcaggtcag gggagtgttg cccgaaaaca ttgagaggaa      60
aacaaaaacc gatgtttgat tgggggaatc ggggggttacg atactaggac gcagtgactg     120
ctatcaccct tggcggtctc ttgttgaaag gaataattac tcta gtg tcg act cac      176
                                                  Val Ser Thr His
                                                   1 aca tct tca acg ctt cca gca ttc aaa aag atc ttg gta gca aac cgc       224
```

| | | |
|---|---|---|
| Thr Ser Ser Thr Leu Pro Ala Phe Lys Lys Ile Leu Val Ala Asn Arg<br>5                              10                   15                      20 | |

```
ggc gaa atc gcg gtc cgt gct ttc cgt gca gca ctc gaa acc ggt gca      272
Gly Glu Ile Ala Val Arg Ala Phe Arg Ala Ala Leu Glu Thr Gly Ala
                 25                  30                  35 gcc acg gta gct att tac ccc cgt gaa gat cgg gga tca ttc cac cgc      320
Ala Thr Val Ala Ile Tyr Pro Arg Glu Asp Arg Gly Ser Phe His Arg
             40                  45                  50 tct ttt gct tct gaa gct gtc cgc att ggt acc gaa ggc tca cca gtc      368
Ser Phe Ala Ser Glu Ala Val Arg Ile Gly Thr Glu Gly Ser Pro Val
         55                  60                  65 aag gcg tac ctg gac atc gat gaa att atc ggt gca gct aaa aaa gtt      416
Lys Ala Tyr Leu Asp Ile Asp Glu Ile Ile Gly Ala Ala Lys Lys Val
     70                  75                  80 aaa gca gat gcc att tac ccg gga tac ggc ttc ctg tct gaa aat gcc      464
Lys Ala Asp Ala Ile Tyr Pro Gly Tyr Gly Phe Leu Ser Glu Asn Ala
 85                  90                  95                 100 cag ctt gcc cgc gag tgt gcg gaa aac ggc att act ttt att ggc cca      512
Gln Leu Ala Arg Glu Cys Ala Glu Asn Gly Ile Thr Phe Ile Gly Pro
                105                 110                 115 acc cca gag gtt ctt gat ctc acc ggt gat aag tct cgc gcg gta acc      560
Thr Pro Glu Val Leu Asp Leu Thr Gly Asp Lys Ser Arg Ala Val Thr
            120                 125                 130 gcc gcg aag aag gct ggt ctg cca gtt ttg gcg gaa tcc acc ccg agc      608
Ala Ala Lys Lys Ala Gly Leu Pro Val Leu Ala Glu Ser Thr Pro Ser
        135                 140                 145 aaa aac atc gat gag atc gtt aaa agc gct gaa ggc cag act tac ccc      656
Lys Asn Ile Asp Glu Ile Val Lys Ser Ala Glu Gly Gln Thr Tyr Pro
    150                 155                 160 atc ttt gtg aag gca gtt gcc ggt ggt ggc gga cgc ggt atg cgt ttt      704
Ile Phe Val Lys Ala Val Ala Gly Gly Gly Gly Arg Gly Met Arg Phe
165                 170                 175                 180 gtt gct tca cct gat gag ctt cgc aaa tta gca aca gaa gca tct cgt      752
Val Ala Ser Pro Asp Glu Leu Arg Lys Leu Ala Thr Glu Ala Ser Arg
                185                 190                 195 gaa gct gaa gcg gct ttc ggc gat ggc gcg gta tat gtc gaa cgt gct      800
Glu Ala Glu Ala Ala Phe Gly Asp Gly Ala Val Tyr Val Glu Arg Ala
            200                 205                 210 gtg att aac cct cag cat att gaa gtg cag atc ctt ggc gat cac act      848
Val Ile Asn Pro Gln His Ile Glu Val Gln Ile Leu Gly Asp His Thr
        215                 220                 225 gga gaa gtt gta cac ctt tat gaa cgt gac tgc tca ctg cag cgt cgt      896
Gly Glu Val Val His Leu Tyr Glu Arg Asp Cys Ser Leu Gln Arg Arg
    230                 235                 240 cac caa aaa gtt gtc gaa att gcg cca gca cag cat ttg gat cca gaa      944
His Gln Lys Val Val Glu Ile Ala Pro Ala Gln His Leu Asp Pro Glu
245                 250                 255                 260 ctg cgt gat cgc att tgt gcg gat gca gta aag ttc tgc cgc tcc att      992
Leu Arg Asp Arg Ile Cys Ala Asp Ala Val Lys Phe Cys Arg Ser Ile
                265                 270                 275 ggt tac cag ggc gcg gga acc gtg gaa ttc ttg gtc gat gaa aag ggc     1040
Gly Tyr Gln Gly Ala Gly Thr Val Glu Phe Leu Val Asp Glu Lys Gly
            280                 285                 290 aac cac gtc ttc atc gaa atg aac cca cgt atc cag gtt gag cac acc     1088
Asn His Val Phe Ile Glu Met Asn Pro Arg Ile Gln Val Glu His Thr
        295                 300                 305 gtg act gaa gaa gtc acc gag gtg gac ctg gtg aag gcg cag atg cgc     1136
Val Thr Glu Glu Val Thr Glu Val Asp Leu Val Lys Ala Gln Met Arg
310                 315                 320
```

```
ttg gct gct ggt gca acc ttg aag gaa ttg ggt ctg acc caa gat aag    1184
Leu Ala Ala Gly Ala Thr Leu Lys Glu Leu Gly Leu Thr Gln Asp Lys
325                 330                 335                 340 atc aag acc cac ggt gca gca ctg cag tgc cgc atc acc acg gaa gat    1232
Ile Lys Thr His Gly Ala Ala Leu Gln Cys Arg Ile Thr Thr Glu Asp
            345                 350                 355 cca aac aac ggc ttc cgc cca gat acc gga act atc acc gcg tac cgc    1280
Pro Asn Asn Gly Phe Arg Pro Asp Thr Gly Thr Ile Thr Ala Tyr Arg
    360                 365                 370 tca cca ggc gga gct ggc gtt cgt ctt gac ggt gca gct cag ctc ggt    1328
Ser Pro Gly Gly Ala Gly Val Arg Leu Asp Gly Ala Ala Gln Leu Gly
375                 380                 385 ggc gaa atc acc gca cac ttt gac tcc atg ctg gtg aaa atg acc tgc    1376
Gly Glu Ile Thr Ala His Phe Asp Ser Met Leu Val Lys Met Thr Cys
        390                 395                 400 cgt ggt tcc gac ttt gaa act gct gtt gct cgt gca cag cgc gcg ttg    1424
Arg Gly Ser Asp Phe Glu Thr Ala Val Ala Arg Ala Gln Arg Ala Leu
405                 410                 415                 420 gct gag ttc acc gtg tct ggt gtt gca acc aac att ggt ttc ttg cgt    1472
Ala Glu Phe Thr Val Ser Gly Val Ala Thr Asn Ile Gly Phe Leu Arg
                425                 430                 435 gcg ttg ctg cgg gaa gag gac ttc act tcc aag cgc atc gcc acc gga    1520
Ala Leu Leu Arg Glu Glu Asp Phe Thr Ser Lys Arg Ile Ala Thr Gly
            440                 445                 450 ttc att gcc gat cac ccg cac ctc ctt cag gct cca cct gct gat gat    1568
Phe Ile Ala Asp His Pro His Leu Leu Gln Ala Pro Pro Ala Asp Asp
    455                 460                 465 gag cag gga cgc atc ctg gat tac ttg gca gat gtc acc gtg aac aag    1616
Glu Gln Gly Arg Ile Leu Asp Tyr Leu Ala Asp Val Thr Val Asn Lys
470                 475                 480 cct cat ggt gtg cgt cca aag gat gtt gca gct cct atc gat aag ctg    1664
Pro His Gly Val Arg Pro Lys Asp Val Ala Ala Pro Ile Asp Lys Leu
485                 490                 495                 500 cct aac atc aag gat ctg cca ctg cca cgc ggt tcc cgt gac cgc ctg    1712
Pro Asn Ile Lys Asp Leu Pro Leu Pro Arg Gly Ser Arg Asp Arg Leu
                505                 510                 515 aag cag ctt ggc cca gcc gcg ttt gct cgt gat ctc cgt gag cag gac    1760
Lys Gln Leu Gly Pro Ala Ala Phe Ala Arg Asp Leu Arg Glu Gln Asp
            520                 525                 530 gca ctg gca gtt act gat acc acc ttc cgc gat gca cac cag tct ttg    1808
Ala Leu Ala Val Thr Asp Thr Thr Phe Arg Asp Ala His Gln Ser Leu
    535                 540                 545 ctt gcg acc cga gtc cgc tca ttc gca ctg aag cct gcg gca gag gcc    1856
Leu Ala Thr Arg Val Arg Ser Phe Ala Leu Lys Pro Ala Ala Glu Ala
550                 555                 560 gtc gca aag ctg act cct gag ctt ttg tcc gtg gag gcc tgg ggc ggc    1904
Val Ala Lys Leu Thr Pro Glu Leu Leu Ser Val Glu Ala Trp Gly Gly
565                 570                 575                 580 gcg acc tac gat gtg gcg atg cgt ttc ctc ttt gag gat ccg tgg gac    1952
Ala Thr Tyr Asp Val Ala Met Arg Phe Leu Phe Glu Asp Pro Trp Asp
                585                 590                 595 agg ctc gac gag ctg cgc gag gcg atg ccg aat gta aac att cag atg    2000
Arg Leu Asp Glu Leu Arg Glu Ala Met Pro Asn Val Asn Ile Gln Met
            600                 605                 610 ctg ctt cgc ggc cgc aac acc gtg gga tac acc ccg tac cca gac tcc    2048
Leu Leu Arg Gly Arg Asn Thr Val Gly Tyr Thr Pro Tyr Pro Asp Ser
    615                 620                 625 gtc tgc cgc gcg ttt gtt aag gaa gct gcc agc tcc ggc gtg gac atc    2096
Val Cys Arg Ala Phe Val Lys Glu Ala Ala Ser Ser Gly Val Asp Ile
630                 635                 640
```

```
ttc cgc atc ttc gac gcg ctt aac gac gtc tcc cag atg cgt cca gca    2144
Phe Arg Ile Phe Asp Ala Leu Asn Asp Val Ser Gln Met Arg Pro Ala
645                 650                 655                 660 atc gac gca gtc ctg gag acc aac acc gcg gta gcc gag gtg gct atg    2192
Ile Asp Ala Val Leu Glu Thr Asn Thr Ala Val Ala Glu Val Ala Met
                665                 670                 675 gct tat tct ggt gat ctc tct gat cca aat gaa aag ctc tac acc ctg    2240
Ala Tyr Ser Gly Asp Leu Ser Asp Pro Asn Glu Lys Leu Tyr Thr Leu
            680                 685                 690 gat tac tac cta aag atg gca gag gag atc gtc aag tct ggc gct cac    2288
Asp Tyr Tyr Leu Lys Met Ala Glu Glu Ile Val Lys Ser Gly Ala His
        695                 700                 705 atc ttg gcc att aag gat atg gct ggt ctg ctt cgc cca gct gcg gta    2336
Ile Leu Ala Ile Lys Asp Met Ala Gly Leu Leu Arg Pro Ala Ala Val
    710                 715                 720 acc aag ctg gtc acc gca ctg cgc cgt gaa ttc gat ctg cca gtg cac    2384
Thr Lys Leu Val Thr Ala Leu Arg Arg Glu Phe Asp Leu Pro Val His
725                 730                 735                 740 gtg cac acc cac gac act gcg ggt ggc cag ctg gca acc tac ttt gct    2432
Val His Thr His Asp Thr Ala Gly Gly Gln Leu Ala Thr Tyr Phe Ala
                745                 750                 755 gca gct caa gct ggt gca gat gct gtt gac ggt gct tcc gca cca ctg    2480
Ala Ala Gln Ala Gly Ala Asp Ala Val Asp Gly Ala Ser Ala Pro Leu
            760                 765                 770 tct ggc acc acc tcc cag cca tcc ctg tct gcc att gtt gct gca ttc    2528
Ser Gly Thr Thr Ser Gln Pro Ser Leu Ser Ala Ile Val Ala Ala Phe
        775                 780                 785 gcg cac acc cgt cgc gat acc ggt ttg agc ctc gag gct gtt tct gac    2576
Ala His Thr Arg Arg Asp Thr Gly Leu Ser Leu Glu Ala Val Ser Asp
    790                 795                 800 ctc gag ccg tac tgg gaa gca gtg cgc gga ctg tac ctg cca ttt gag    2624
Leu Glu Pro Tyr Trp Glu Ala Val Arg Gly Leu Tyr Leu Pro Phe Glu
805                 810                 815                 820 tct gga acc cca ggc cca acc ggt cgc gtc tac cgc cac gaa atc cca    2672
Ser Gly Thr Pro Gly Pro Thr Gly Arg Val Tyr Arg His Glu Ile Pro
                825                 830                 835 ggc gga cag ttg tcc aac ctg cgt gca cag gcc acc gca ctg ggc ctt    2720
Gly Gly Gln Leu Ser Asn Leu Arg Ala Gln Ala Thr Ala Leu Gly Leu
            840                 845                 850 gcg gat cgt ttc gaa ctc atc gaa gac aac tac gca gcc gtt aat gag    2768
Ala Asp Arg Phe Glu Leu Ile Glu Asp Asn Tyr Ala Ala Val Asn Glu
        855                 860                 865 atg ctg gga cgc cca acc aag gtc acc cca tcc tcc aag gtt gtt ggc    2816
Met Leu Gly Arg Pro Thr Lys Val Thr Pro Ser Ser Lys Val Val Gly
    870                 875                 880 gac ctc gca ctc cac ctc gtt ggt gcg ggt gtg gat cca gca gac ttt    2864
Asp Leu Ala Leu His Leu Val Gly Ala Gly Val Asp Pro Ala Asp Phe
885                 890                 895                 900 gct gcc gat cca caa aag tac gac atc cca gac tct gtc atc gcg ttc    2912
Ala Ala Asp Pro Gln Lys Tyr Asp Ile Pro Asp Ser Val Ile Ala Phe
                905                 910                 915 ctg cgc ggc gag ctt ggt aac cct cca ggt ggc tgg cca gag cca ctg    2960
Leu Arg Gly Glu Leu Gly Asn Pro Pro Gly Gly Trp Pro Glu Pro Leu
            920                 925                 930 cgc acc cgc gca ctg gaa ggc cgc tcc gaa ggc aag gca cct ctg acg    3008
Arg Thr Arg Ala Leu Glu Gly Arg Ser Glu Gly Lys Ala Pro Leu Thr
        935                 940                 945 gaa gtt cct gag gaa gag cag gcg cac ctc gac gct gat gat tcc aag    3056
Glu Val Pro Glu Glu Glu Gln Ala His Leu Asp Ala Asp Asp Ser Lys
```

-continued

```
                      950                 955                 960
gaa cgt cgc aat agc ctc aac cgc ctg ctg ttc ccg aag cca acc gaa        3104
Glu Arg Arg Asn Ser Leu Asn Arg Leu Leu Phe Pro Lys Pro Thr Glu
965                 970                 975                 980 gag ttc ctc gag cac cgt cgc cgc ttc ggc aac acc tct gcg ctg gat        3152
Glu Phe Leu Glu His Arg Arg Arg Phe Gly Asn Thr Ser Ala Leu Asp
                985                 990                 995 gat cgt gaa ttc ttc tac ggc ctg gtc gaa ggc cgc gag act ttg atc        3200
Asp Arg Glu Phe Phe Tyr Gly Leu Val Glu Gly Arg Glu Thr Leu Ile
            1000                1005                1010 cgc ctg cca gat gtg cgc acc cca ctg ctt gtt cgc ctg gat gcg atc        3248
Arg Leu Pro Asp Val Arg Thr Pro Leu Leu Val Arg Leu Asp Ala Ile
        1015                1020                1025 tct gag cca gac gat aag ggt atg cgc aat gtt gtg gcc aac gtc aac        3296
Ser Glu Pro Asp Asp Lys Gly Met Arg Asn Val Val Ala Asn Val Asn
    1030                1035                1040 ggc cag atc cgc cca atg cgt gtg cgt gac cgc tcc gtt gag tct gtc        3344
Gly Gln Ile Arg Pro Met Arg Val Arg Asp Arg Ser Val Glu Ser Val
1045                1050                1055                1060 acc gca acc gca gaa aag gca gat tcc tcc aac aag ggc cat gtt gct        3392
Thr Ala Thr Ala Glu Lys Ala Asp Ser Ser Asn Lys Gly His Val Ala
                1065                1070                1075 gca cca ttc gct ggt gtt gtc acc gtg act gtt gct gaa ggt gat gag        3440
Ala Pro Phe Ala Gly Val Val Thr Val Thr Val Ala Glu Gly Asp Glu
            1080                1085                1090 gtc aag gct gga gat gca gtc gca atc atc gag gct atg aag atg gaa        3488
Val Lys Ala Gly Asp Ala Val Ala Ile Ile Glu Ala Met Lys Met Glu
        1095                1100                1105 gca aca atc act gct tct gtt gac ggc aaa atc gat cgc gtt gtg gtt        3536
Ala Thr Ile Thr Ala Ser Val Asp Gly Lys Ile Asp Arg Val Val Val
    1110                1115                1120 cct gct gca acg aag gtg gaa ggt ggc gac ttg atc gtc gtc gtt tcc        3584
Pro Ala Ala Thr Lys Val Glu Gly Gly Asp Leu Ile Val Val Val Ser
1125                1130                1135                1140 taa acctttctgt aaaaagcccc gcgtcttcct catggaggag gcggggcttt             3637
ttgggccaag atgggagatg ggtgagttgg atttggtctg attcgacact tttaagggca     3697
gagatttgaa gatggagacc aaggctcaaa g                                      3728
```

<210> SEQ ID NO 2
<211> LENGTH: 1140
<212> TYPE: PRT
<213> ORGANISM: Corynebacterium glutamicum

<400> SEQUENCE: 2

```
Val Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
```

-continued

```
                100                 105                 110
Phe Ile Gly Pro Thr Pro Glu Val Leu Asp Leu Thr Gly Asp Lys Ser
            115                 120                 125

Arg Ala Val Thr Ala Ala Lys Lys Ala Gly Leu Pro Val Leu Ala Glu
        130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525
```

-continued

```
Arg Glu Gln Asp Ala Leu Ala Val Thr Asp Thr Thr Phe Arg Asp Ala
    530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
        595                 600                 605
Asn Ile Gln Met Leu Leu Arg Gly Arg Asn Thr Val Gly Tyr Thr Pro
    610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
        675                 680                 685
Leu Tyr Thr Leu Asp Tyr Tyr Leu Lys Met Ala Glu Glu Ile Val Lys
    690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
Thr Tyr Phe Ala Ala Ala Gln Ala Gly Ala Asp Ala Val Asp Gly Ala
        755                 760                 765
Ser Ala Pro Leu Ser Gly Thr Thr Ser Gln Pro Ser Leu Ser Ala Ile
    770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
                805                 810                 815
Leu Pro Phe Glu Ser Gly Thr Pro Gly Pro Thr Gly Arg Val Tyr Arg
            820                 825                 830
His Glu Ile Pro Gly Gly Gln Leu Ser Asn Leu Arg Ala Gln Ala Thr
        835                 840                 845
Ala Leu Gly Leu Ala Asp Arg Phe Glu Leu Ile Glu Asp Asn Tyr Ala
    850                 855                 860
Ala Val Asn Glu Met Leu Gly Arg Pro Thr Lys Val Thr Pro Ser Ser
865                 870                 875                 880
Lys Val Val Gly Asp Leu Ala Leu His Leu Val Gly Ala Gly Val Asp
                885                 890                 895
Pro Ala Asp Phe Ala Ala Asp Pro Gln Lys Tyr Asp Ile Pro Asp Ser
            900                 905                 910
Val Ile Ala Phe Leu Arg Gly Glu Leu Gly Asn Pro Pro Gly Gly Trp
        915                 920                 925
Pro Glu Pro Leu Arg Thr Arg Ala Leu Glu Gly Arg Ser Glu Gly Lys
    930                 935                 940
```

-continued

```
Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Pro Ala Ala Thr Lys Val Glu Gly Gly Asp Leu Ile
                1125                1130                1135

Val Val Val Ser
            1140

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 3
cgtcttcatc gaaatgaac                                              19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 4
acggtggtga tccggcact                                              19
```